(12) United States Patent
Fujimoto

(10) Patent No.: US 6,373,915 B1
(45) Date of Patent: Apr. 16, 2002

(54) EXCHANGE JIG, BED DEVICE, AND X-RAY COMPUTED TOMOGRAPHY APPARATUS

(75) Inventor: Hideki Fujimoto, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/534,395

(22) Filed: Mar. 24, 2000

(30) Foreign Application Priority Data

Mar. 26, 1999 (JP) ............................................ 11-084335

(51) Int. Cl.[7] ................................................ G01N 23/00
(52) U.S. Cl. .......................................... 378/4; 378/195
(58) Field of Search ............................ 378/4, 195, 198; 5/600; 600/215, 216, 217

(56) References Cited

U.S. PATENT DOCUMENTS

| 5,555,897 A | * | 9/1996 | Lathrop, Jr. et al. | 128/847 |
| 5,592,153 A | * | 1/1997 | Welling et al. | 340/825.19 |
| 6,012,456 A | * | 1/2000 | Schuerch | 128/869 |
| 6,031,888 A | * | 2/2000 | Ivan et al. | 378/20 |

FOREIGN PATENT DOCUMENTS

| JP | 06014919 A | * | 1/1994 | ............ A61B/5/04 |
| JP | 6-254083 | | 9/1994 | |
| JP | 8-164133 | | 6/1996 | |

* cited by examiner

Primary Examiner—Robert H. Kim
Assistant Examiner—Irakli Kiknadze
(74) Attorney, Agent, or Firm—Oblon, Spivak, McClelland, Maier & Neustadt, P.C.

(57) ABSTRACT

This invention provides an exchange jig for assisting work of exchanging a heavy object such as an X-ray tube. This exchange jig has a detachable unit, which enables attaching/detaching the exchange jig to/from the top plate of a bed. In exchange work, the exchange jig is attached to the top plate of the bed. The elevating function and top plate slide function of the bed realize a forklift function together with the support function of the arm unit of the exchange jig. If exchange work is not performed, the exchange jig can be detached from the top plate of the bed. The arm unit is attached to the detachable unit through a rotating unit. The rotating unit freely rotates about an almost vertical axis. This rotation facilitates work of transferring the heavy object between the arm unit and a gantry, and work of transferring the heavy object between the arm unit and a truck.

20 Claims, 5 Drawing Sheets

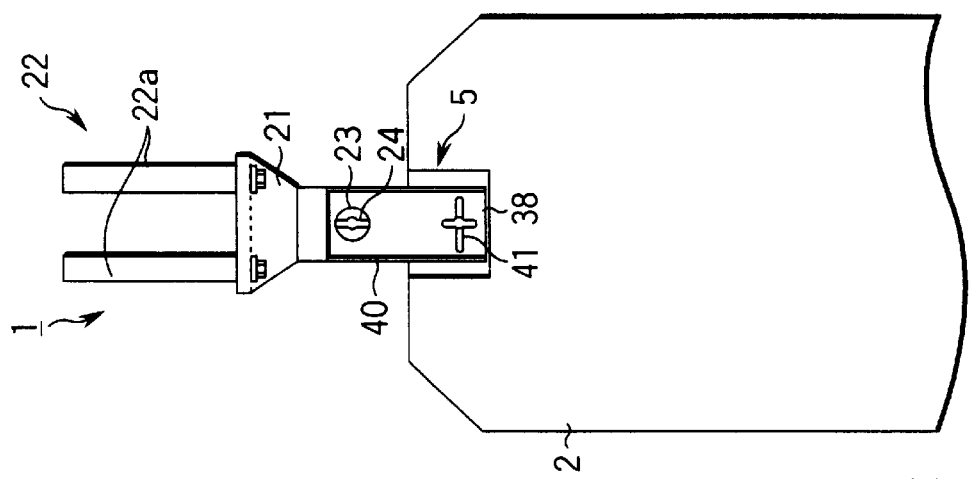
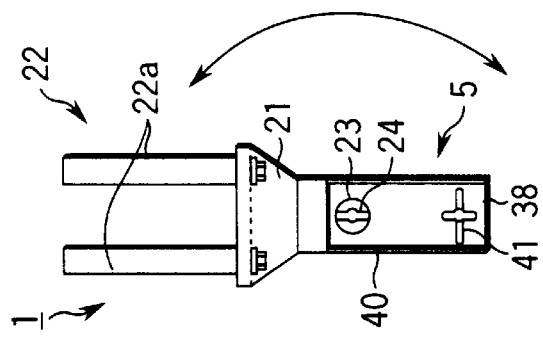
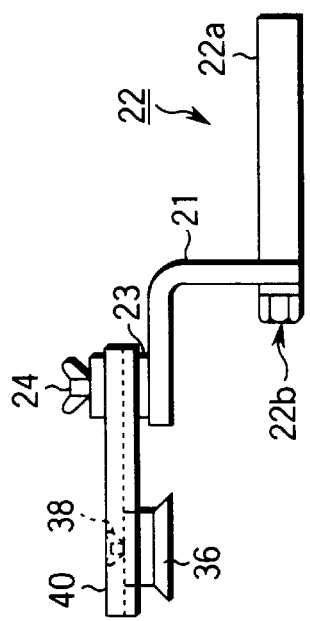
FIG. 6C
FIG. 6B
FIG. 6A

EXCHANGE JIG, BED DEVICE, AND X-RAY COMPUTED TOMOGRAPHY APPARATUS

CROSS-REFERENCE TO RELATED APPLICATIONS

This application i s based upon and claims the benefit of priority from the prior Japanese Patent Application No. 11-084335, filed Mar. 26, 1999, the entire contents of which are incorporated herein by reference.

BACKGROUND OF THE INVENTION

The present invention relates to an exchange jig for a heavy object such as an X-ray tube incorporated in the gantry of a medical image sensing apparatus such as an X-ray computed tomography apparatus (X-ray CT) or magnetic resonance imaging apparatus (MRI), a bed device, and an X-ray computed tomography.

FIG. 1A is a sectional view showing the gantry of a conventional X-ray computed tomography apparatus. A gantry frame 41 supports a rotating ring 42. The rotating ring 42 can rotate. An X-ray tube 44, high-voltage generator 45, X-ray detector 46, and the like are mounted on the rotating ring 42.

The X-ray tube 44 is as heavy as 25 kg for a light tube and 65 kg for a heavy tube. The high-voltage generator 45 and X-ray detector 46 are also heavy. Exchange work of dismounting an old X-ray tube from the rotating ring 42 and mounting a new one is very hard work. To assist this exchange work, the gantries of most conventional X-ray computed tomography apparatuses incorporate exchange jigs (crane mechanisms) for assisting work of exchanging an old X-ray tube or the like with a new one.

A column 50 of an exchange jig 48 is attached almost perpendicularly to, e.g., a holder 49 of the gantry frame 41. The column 50 is coupled to an almost horizontal arm 51. A reel 53 hangs from the distal end of the arm 51. A hook 52b is connected to the end of a wire 55 of the reel 53.

In exchange work, an old X-ray tube 44 is tied with a rope 54, which is hooked on the hook 52b. The X-ray tube 44 is dismounted from the rotating ring 42, and pulled up by the reel 53. As shown in FIG. 1B, the column 50 is axially rotated to remove the X-ray tube 44 outside the gantry. The X-ray tube 44 is put down on the floor by the reel 53. The X-ray tube 44 is released from the rope 54, and loaded on a truck. A new X-ray tube 44 is mounted in a reverse order to the dismounting order.

FIG. 2A shows another exchange jig 61. A slide rail 61a is almost horizontally attached to a gantry frame 41. A slide frame 61b can slide along the slide rail 61a. A hook 63 hangs from the reel 65 of the distal end of the slide frame 61b.

In exchanging an X-ray tube 44, a rope 64 which ties an old X-ray tube 44 is hooked on the hook 63. The slide frame 61b is slid and the reel 65 is lowered, to remove the X-ray tube 44 outside the gantry frame 41. Then, the X-ray tube 44 is loaded on a transport truck. A new X-ray tube 44 is mounted in a reverse order to the dismounting order.

As described above, the gantries of most conventional X-ray computed tomography apparatuses incorporate exchange jigs. This is one of factors that enlarge the gantry.

Since the rotation radius of the arm 51 and the slide length of the exchange jig 61 are short, the X-ray tube cannot be directly loaded from the exchange jig on the truck. The X-ray tube must be temporarily put down on the floor, and then loaded from the floor on the truck. This decreases the workability, and may inhibit exchange work using the exchange jig in a small CT room.

BRIEF SUMMARY OF THE INVENTION

It is an object of the present invention to simplify exchange work of a heavy object such as an X-ray tube.

The present invention provides an exchange jig for assisting work of exchanging a heavy object such as an X-ray tube. This exchange jig has a detachable unit, which enables attaching/detaching the exchange jig to/from the top plate of a bed. In exchange work, the exchange jig is attached to the top plate of the bed. The elevating function and top plate slide function of the bed realize a forklift function together with the support function of the arm unit of the exchange jig. If exchange work is not performed, the exchange jig can be detached from the top plate of the bed. The arm unit is attached to the detachable unit through a rotating unit. The rotating unit freely rotates about an almost vertical axis. This rotation facilitates work of transferring the heavy object between the arm unit and a gantry, and work of transferring the heavy object between the arm unit and a truck.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 6A is a side view showing an exchange jig in the third embodiment of the present invention;

FIG. 6B is a plan view showing the exchange jig in the third embodiment; and

FIG. 6C is a plan view showing the exchange jig attached to the headrest mount of a top plate in the third embodiment.

DETAILED DESCRIPTION OF THE INVENTION

The gist of the present invention is to use a bed as a forklift by attaching an exchange jig to the top plate of the bed. That is, the bed functions as a forklift with the support function of the arm unit of the exchange jig in addition to the elevating function and top plate slide function of the bed. Preferred embodiments of the present invention will be described in detail below.

First Embodiment

Figure 1A:
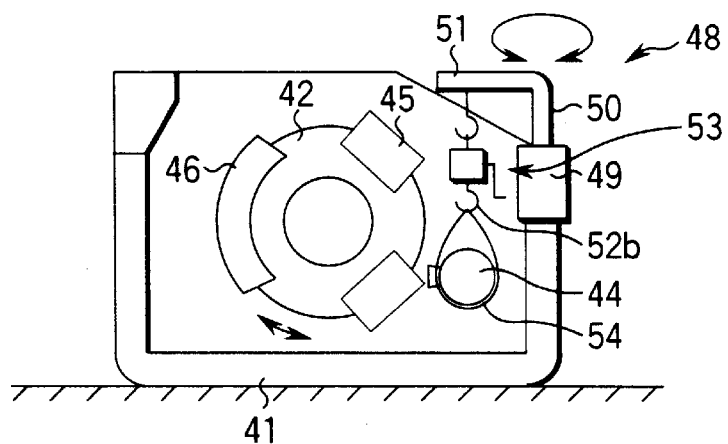
FIGS. 1A and 1B are views showing a conventional exchange jig incorporated in the gantry of an X-ray computed tomography apparatus.
Figure 1B:
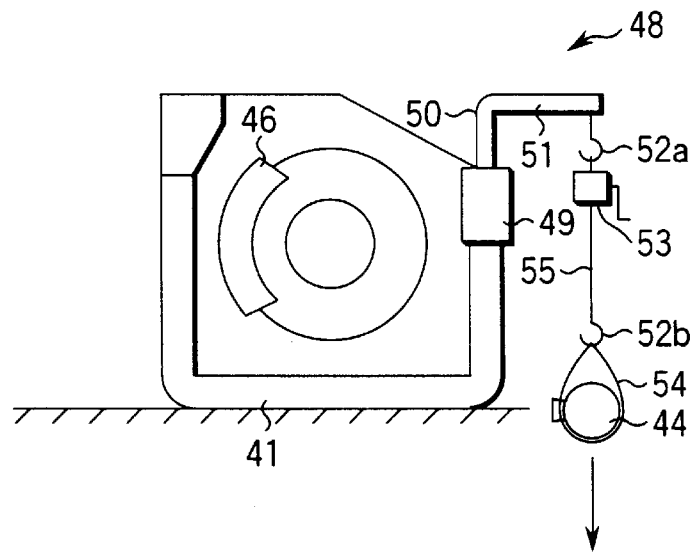
Figure 2A:
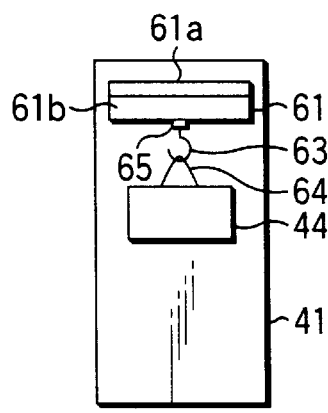
FIGS. 2A and 2B are views showing another conventional exchange jig incorporated in the gantry of an X-ray computed tomography apparatus.
Figure 2B:
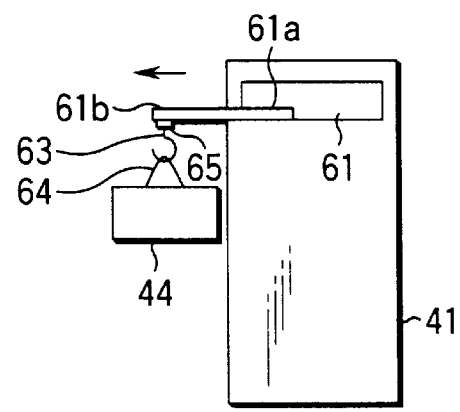
Figure 3A:
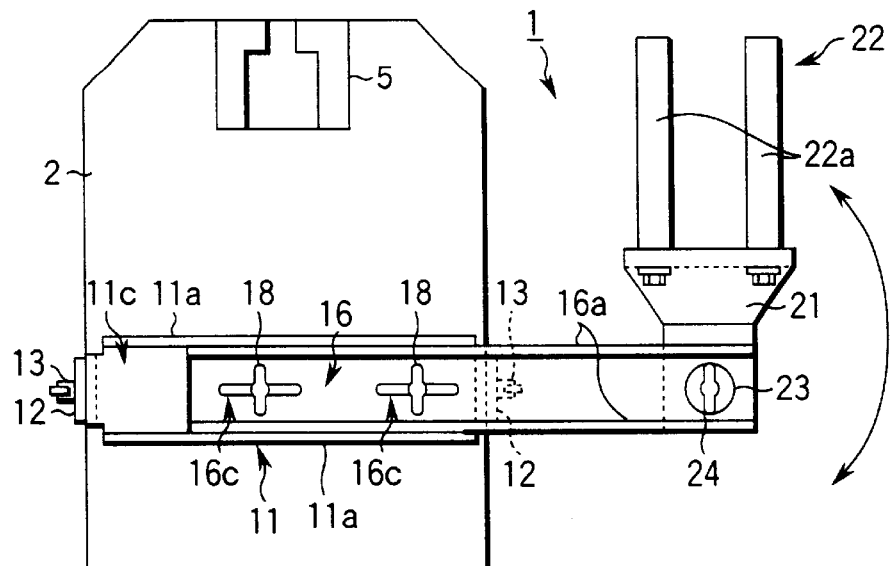
FIG. 3A is a plan view showing an exchange jig attached to the top plate of a bed according to the first embodiment of the present invention.
Figure 3B:
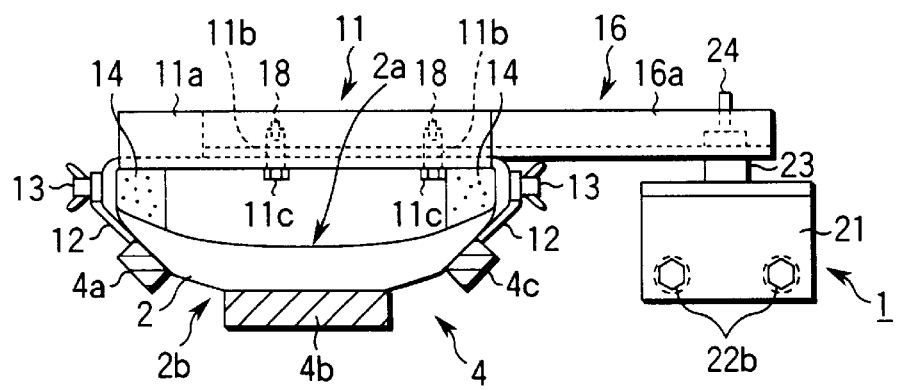
FIG. 3B is a front view showing the exchange jig attached to the top plate of the bed according to the first embodiment.
Figure 3C:
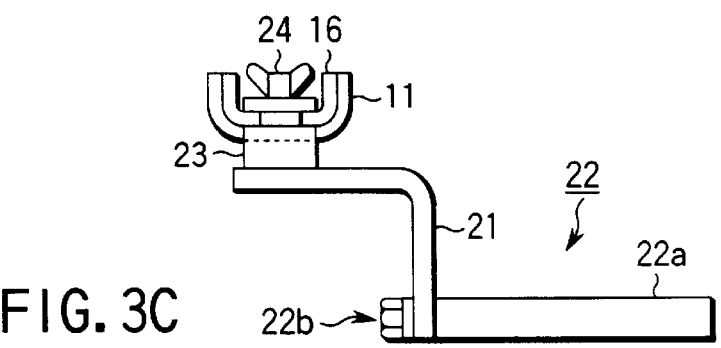
FIG. 3C is a side view showing the exchange jig in the first embodiment.

FIGS. 3A to 3C show the structure of an exchange jig according to the first embodiment of the present invention. An exchange jig 1 is detachable from a top plate 2 of a bed. The bed comprises a slide mechanism for slidably supporting the top plate 2 in a longitudinal direction, and an elevating mechanism for elevating the top plate 2.

[Structure of Top Plate]

As shown in FIG. 3B, the top plate 2 has an almost semi-arcuated sectional shape. An upper surface 2a of the top plate 2 on which a patient lies is formed into an arcuated recessed shape. As shown in FIG. 3A, a headrest mount 5 for mounting a headrest for resting a patient's head is formed at one end of the mounting surface 2a.

A lower surface 2b of the top plate 2 is formed into an arcuated projecting shape. The top plate 2 is supported slidably in the longitudinal direction of the top plate by a main roller 4b arranged immediately below the top plate 2 and sub-rollers 4a and 4c arranged at the left and right edges of the top plate 2. The sub-rollers 4a and 4c are newly added to prevent distortion and rolling of the top plate 2 under a heavy load from the left and right upon mounting the exchange jig 1.

[Structure of Exchange Jig]

The exchange jig 1 comprises a detachable unit 11 detachable from the top plate 2, the slide rail 16 attached to the unit 11, a rotating unit 21 attached to the detachable unit 11 rotatably about an almost vertical axis, and an arm unit 22 attached to the rotating unit 21 to support a heavy object such as an X-ray tube, a high-voltage generating unit and a X-ray detector.

[Structure of Detachable Unit]

The detachable unit 11 has a frame 11a mounted on the top plate 2, and a slide rail 16 supported by the frame 11a slidably in the widthwise direction of the top plate. The frame 11a has an almost equal length to the width of the top plate 2, and has a U sectional shape, as shown in FIG. 3C. The slide rail 16 is fitted in the frame 11a.

Holding members 12 for holding the top plate 2 together with the frame 11a are attached to the two ends of the frame 11a with wing nuts 13 and threaded blocks 14. Each threaded block 14 is curved to conform to the shape of the upper surface 2a of the top plate 2. The frame 11a is set at an arbitrary position on the top plate 2, and the wing nuts 13 are screwed into the threaded blocks 14 to tightly sandwich the top plate 2 between the holding members 12 and the threaded blocks 14. Accordingly, the frame 11a can be fixed to an arbitrary position on the top plate 2. The threaded block 14 prevents damage to the upper surface 2a of the top plate 2 and suppresses distortion of the top plate 2.

[Structure of Slide Rail]

The slide rail 16 is longer than the frame 11a. The slide rail 16 has two slits 16c. Wing nuts 18 are screwed into nuts 11c through the slits 16c of the slide rail 16 and holes 11b formed in the frame 11a. Loosing the wing nut 18 allows the slide rail 16 to slide within the range of the slit 16c. Securely tightening the wing nut 18 fixes the slide rail 16 to the frame 11a.

[Structure of Rotating Unit]

The rotating unit 21 is attached to the distal end of the slide rail 16 through a spacer 23 rotatably about an almost vertical axis. The distal end of a wing nut 24 is screwed into the threaded hole of the rotating unit 21 through the hole of the distal end of the slide rail 16 and the hole of the spacer 23. Loosing the wing nut 24 allows the rotating unit 21 to freely rotate on the slide rail 16. Securely tightening the wing nut 24 fixes the rotating unit 21 to the slide rail 16. The rotating unit 21 has an almost L shape, and the arm unit 22 is attached to the lower portion of the vertical surface of the L-shaped rotating unit 21. The L-shaped rotating unit 21 can hold arms 22a at lower positions than the upper surface 2a of the top plate 2 together with the spacer 23. This makes it possible to put down a heavy object such as an X-ray tube on a lower position than the lowest position of the top plate 2. The heavy object can be easily transferred between the arm unit 22 and a truck.

[Structure of Arm Unit]

The arm unit 22 has a pair of arms 22a. The arms 22a have a columnar shape and are coated with an elastic material such as rubber so as not to damage an object to be mounted. The pair of arms 22a are attached perpendicularly to the rotating unit 21 to be parallel to each other at a predetermined interval, like tips of a fork. The arm 22a can take various lengths and thicknesses. The arm 22a is detachable from the rotating unit 21 by a bolt 22b so as to be exchanged with an arm having a length and thickness corresponding to the shape and weight of an object to be mounted.

Operation of First Embodiment

Exchange operation of a predetermined unit of the bed device having this structure according to the first embodiment will be described. An X-ray computed tomography apparatus will be exemplified. As is well known, the X-ray computed tomography apparatus is constituted by a bed on which an object to be examined lies, a gantry for collecting projection data about the object, and a computer for reconstructing tomographic image data based on the collected projection data. The gantry has a rotating ring which rotates about an almost horizontal axis. The rotating ring holds an X-ray tube, a high-voltage generator for applying a high voltage to the X-ray tube, an X-ray detector for detecting X-rays having passed through the object, and other components. The X-ray tube, high-voltage generator, and X-ray detector are heavier than other components. Hence, exchange work of the X-ray tube, high-voltage generator, and X-ray detector requires assistance of the exchange jig. In particular, the exchange jig is indispensable for exchange work of the heaviest X-ray tube. In this case, exchange work of the X-ray tube will be exemplified.

(Mounting of Exchange Jig)

The frame 11a is located at a desired position on the top plate 2, and the wing nut 13 is tightened to fix the frame 11a to the top plate 2. The slide rail 16 is slid to project from the frame 11a by a desired length. The wing nuts 18 are tightened to fix the slide rail 16 to the frame 11a. The arms 22a are rotated and fixed to the rotating unit 21 in a desired direction.

(Exchange Work)

Figure 4A:
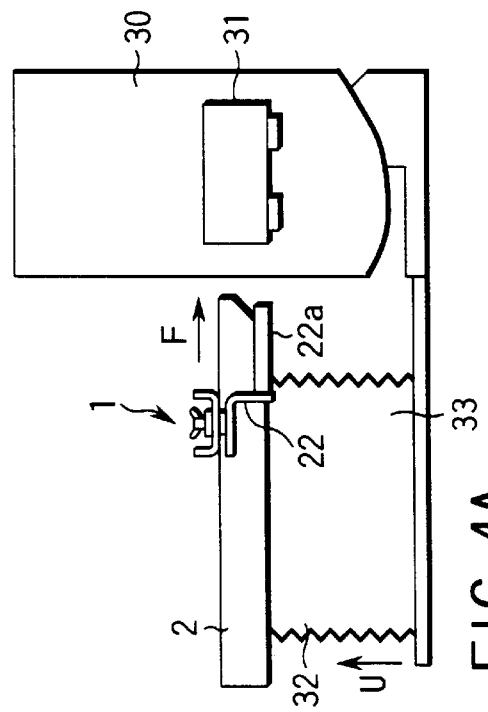
FIGS. 4A to 4D are views showing X-ray tube dismounting work procedures in the first embodiment.
Figure 4B:
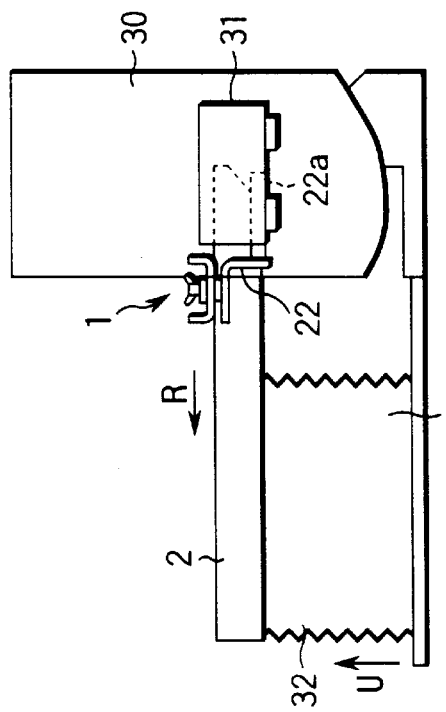

The gantry cover of the X-ray computed tomography apparatus is removed. As shown in FIG. 4A, an X-ray tube 31 in a gantry 30 is moved, e.g., from a position immediately above the top plate 2 to a position rotated through 90°. The top plate 2 is properly elevated by the operation of an elevating mechanism 32 of the bed. The arms 22a of the exchange jig 1 are then located at positions slightly lower than the bottom of the X-ray tube 31. As shown in FIG. 4B, the top plate 2 is properly slid in a forward direction F by the operation of a slide mechanism 33 of the bed. Accordingly, the arms 22a of the exchange jig 1 are located immediately below the X-ray tube 31. The top plate 2 is slightly moved up by the operation of the elevating mechanism 32. The X-ray tube 31 is brought into contact with the arms 22a of the exchange jig 1. In this state, the X-ray tube 31 is detached from the rotating ring and completely mounted on the arms 22a of the exchange jig 1.

Figure 4C:
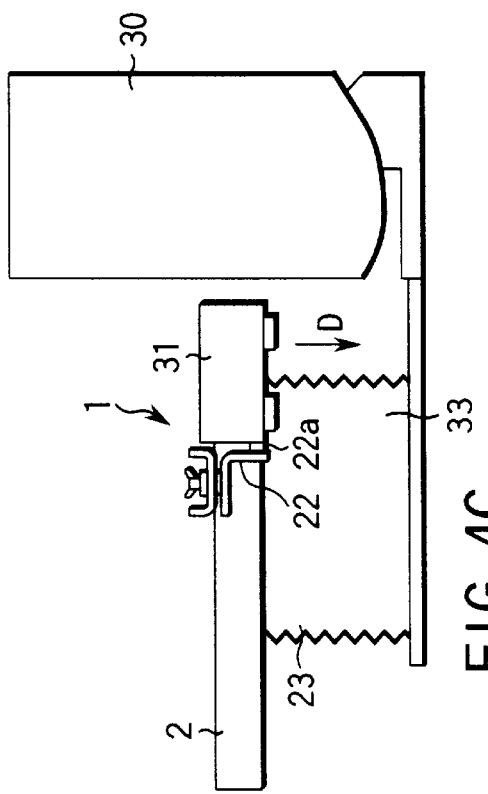

The top plate 2 is slightly slid in a backward direction R by the operation of the slide mechanism 33. As shown in FIG. 4C, the X-ray tube 31 is removed outside the gantry 30. Since the arms 22a are located on the side of the top plate 2, the top plate 2 may be distorted by the weight of the X-ray tube 31 upon supporting the X-ray tube 31 by the arms 22a. However, the two sides of the top plate 2 are supported by the sub-rollers 4a and 4c, so the top plate 2 does not distort.

Figure 4D:
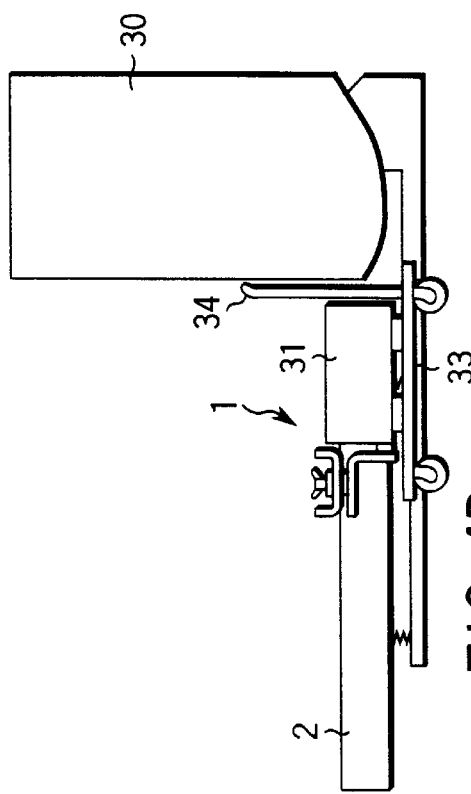

After the X-ray tube 31 is removed outside the gantry 30, the top plate 2 is moved down in a downward direction D by the operation of the elevating mechanism 32. As shown in FIG. 4D, the X-ray tube 31 is put down on a truck 34. Since the arms 22a are located at lower positions than the lowest position of the top plate 2 by the rotating unit 21 and spacer 23, as described above, a heavy object such as the X-ray tube can be directly loaded on the truck 34.

In attaching a new X-ray tube, it is loaded by the truck 34, and the above-described procedures are executed in a reverse order from FIG. 4D→FIG. 4C→FIG. 4B→FIG. 4A. More specifically, the support arm unit 22 is moved down to flush with the transport truck 34, the new X-ray tube is placed on the arms 22a, and the arms 22a are moved up to a predetermined level. In this state, the arms 22a are slid toward the gantry 30. Accordingly, the new X-ray tube can be easily attached to the rotating ring in the gantry 30.

Effect of First Embodiment

As is apparent from the above description, since the bed can function as a forklift by attaching the exchange jig to the bed, exchange work can be done in a small exchange space accurately, safely, and easily. Since no exchange jig need be incorporated in the gantry, the gantry can be downsized. Since the sub-rollers attached to the bed prevent distortion of the top plate, damage to the bed can be prevented, and the safety of exchange work can be improved.

Second Embodiment

In the first embodiment, the exchange jig is attached to the top plate 2 through the frame 11a. In the second embodiment, the exchange jig is attached to a headrest mount which exists on the top plates of most beds. Note that the first and second embodiments are different only in this point, only the different feature will be described, and a repetitive description thereof will be omitted.

Structure of Second Embodiment

Figure 5A:
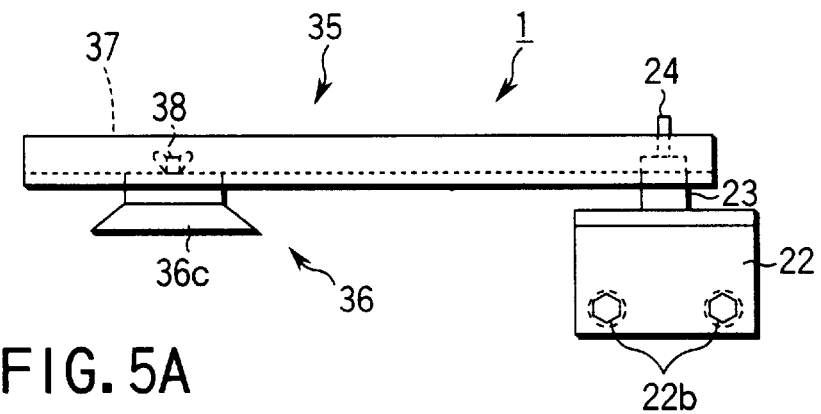
FIG. 5A is a side view showing an exchange jig in the second embodiment of the present invention.
Figure 5B:
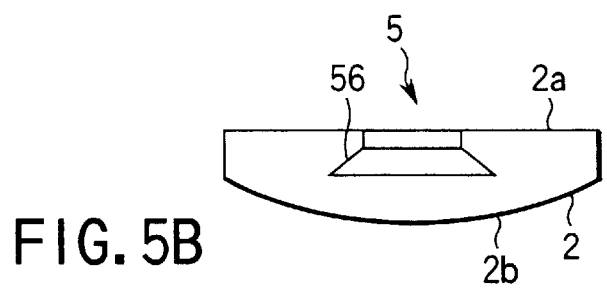
FIG. 5B is a sectional view showing the headrest mount of a top plate in the second embodiment.
Figure 5C:
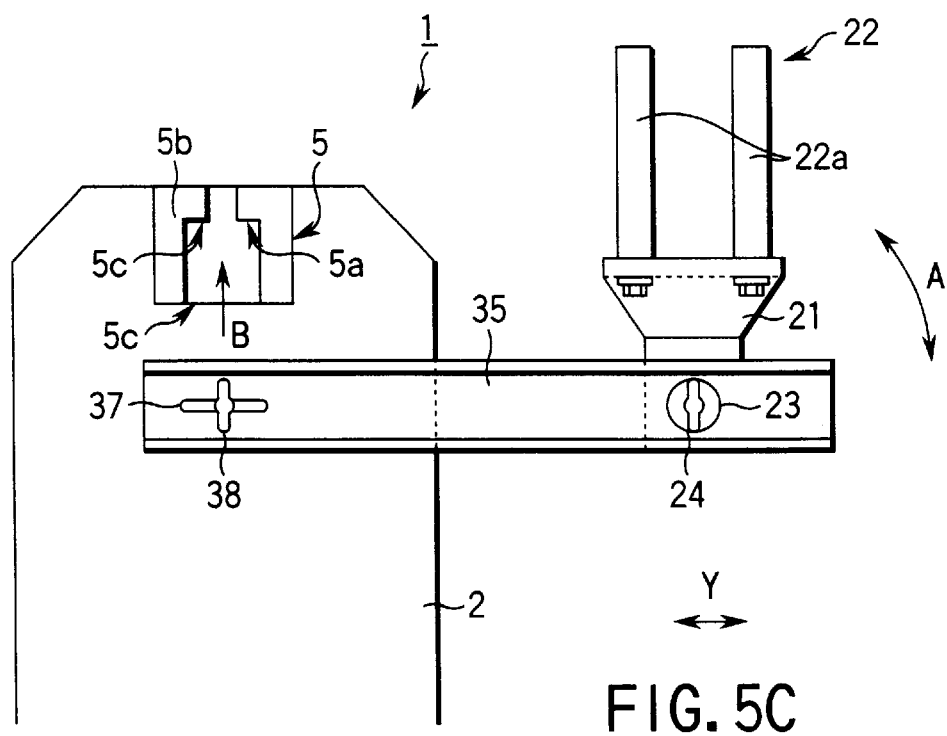
FIG. 5C is a plan view showing the exchange jig attached to the headrest mount of the top plate in the second embodiment.

FIGS. 5A to 5C show the structure of an exchange jig according to the second embodiment. In an exchange jig 1 of the second embodiment, a fitting portion 36 to be fitted in a headrest mount 5 of a top plate 2 is attached to one end of a slide rail 35 having an almost U sectional shape. The headrest mount 5 of the top plate 2 has an almost trapezoidal cross section. The fitting portion 36 is formed into an almost trapezoidal shape so as to be fitted in the headrest mount 5. This effectively prevents the fitting portion 36 from slipping off upward and laterally from the headrest mount 5. Stoppers 5a of the headrest mount 5 effectively prevent the fitting portion 36 from slipping off forward from the headrest mount 5.

A wing nut 38 is screwed into the threaded hole of the fitting portion 36 through a slit 37 formed in the slide rail 35. Loosening the wing nut 38 allows the slide rail 35 to slide on the fitting portion 36 and top plate 2 in a widthwise direction Y of the top plate 2. Securely tightening the wing nut 38 fixes the slide rail 35 to the fitting portion 36 and top plate 2.

Operation of Second Embodiment

The fitting portion 36 of the exchange jig 1 is fitted in the headrest mount 5 of the top plate 2. The slide rail 35 is appropriately slid within the range of the slit 37. The wing nut 38 is tightened at a position where the slide rail 35 projects from the top plate 2 by a proper length, thereby fixing the slide rail 35 to the top plate 2. Arms 22a are appropriately rotated, and a wing nut 24 is tightened and fixed in a proper direction.

The subsequent exchange procedures are the same as in the first embodiment.

Effect of Second Embodiment

As is apparent from the above description, the bed device of the second embodiment can use the headrest mount 5 of the top plate 2 to attach the exchange jig 1. Therefore, the exchange jig 1 can be attached to the top plate 2 without using the frame 11a described in the first embodiment. The second embodiment can simplify the structure and decrease the number of components to reduce the cost. In addition, the second embodiment can attain the same effects as those of the first embodiment.

Structure of Third Embodiment

FIGS. 6A to 6C show the structure of an exchange jig according to the third embodiment. In an exchange jig 1 of the third embodiment, a short frame 40 is attached to a fitting portion 36a fitted in a headrest mount 5 of a top plate 2. A rotating unit 21 and arm unit 22 are attached to the distal end of the short frame 40. In the second embodiment, the slide frame is arranged to cross the top plate 2. In the third embodiment, the short frame 40 is arranged parallel to the longitudinal direction of the top plate 2. That is, the short frame 40 is arranged not on the side of the top plate 2 but in front of it.

A wing nut 38 is screwed in the threaded hole of the fitting portion 36a through a slit 41 formed in the frame 40. Loosening the wing nut 38 allows the frame 40 to slightly slide on the fitting portion 36 and top plate 2 by the length of the slit 41 in a widthwise direction Y of the top plate 2. Securely tightening the wing nut 38 fixes the frame 40 to the fitting portion 36 and top plate 2.

Operation of Third Embodiment

The fitting portion 36a of the exchange jig 1 is fitted in the headrest mount 5 of the top plate 2. The frame 40 is appropriately slid to the right and left within the range of the gantry frame 41. The wing nut 38 is tightened to fix the frame 40 to the top plate 2. Arms 22a are appropriately rotated, and a wing nut 24 is tightened and fixed in a proper direction.

The subsequent exchange procedures are the same as in the first embodiment.

Effect of Third Embodiment

As is apparent from the above description, the bed device of the third embodiment can use the headrest mount 5 of the top plate 2 to attach the exchange jig 1. The exchange jig 1 can be attached to the top plate 2 without using the frame 11a described in the first embodiment. The third embodiment can simplify the structure and decrease the number of components to reduce the cost. Since the frame 40 is short, the exchange jig can be downsized. Further, since the arms 22a can be arranged on the central axis of the top plate 2, the load on the top plate 2 can be reduced.

Modification

The above-mentioned embodiments are merely examples of the present invention, and do not limit the present invention. For example, in the above-mentioned embodiments, the bed device according to the present invention is applied to the bed of an X-ray computed tomography apparatus, but may be applied to the bed of another modality such as an MRI apparatus or X-ray diagnostic apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. In a medical imaging device having a bed and at least one operational component, an exchange jig comprising:
    a detachable unit configured to be detachably coupled to a top plate of the bed;
    a rotating unit attached to said detachable unit and configured to rotate about an axis substantially perpendicular to an axis parallel to the top plate; and
    an arm unit attached to said rotating unit,
    wherein a movement of the top plate moves the exchange jig such that the arm unit operates as a lift to exchange the at least one operational component.

2. A jig according to claim 1, further comprising a slide mechanism configured to slide said rotating unit in a widthwise direction of the top plate.

3. A jig according to claim 1, wherein said arm unit has a fork-shape.

4. A jig according to claim 1, wherein said arm unit has a columnar shape.

5. A jig according to claim 1, wherein said arm unit comprises an elastic material coating.

6. A jig according to claim 1, wherein said arm unit can directly set to a heavy object of said rotating unit.

7. A jig according to claim 1, wherein said arm unit is detachably connected to said rotating unit.

8. A jig according to claim 1, wherein said arm unit is located at a position lower than an upper surface of the top plate.

9. A jig according to claim 1, further comprising a fixing unit configured to stop a rotation of said rotating unit with respect to said detachable unit.

10. A jig according to claim 1, wherein said detachable unit comprises a frame which crosses the top plate, and a holding member configured to hold the top plate together with said frame.

11. A jig according to claim 10, wherein said detachable unit comprises a slide frame attached to said frame and configured to slide in a widthwise direction of the top plate, and wherein said rotating unit is attached to said slide frame.

12. A jig according to claim 11, further comprising a fixing unit configured to stop a sliding of said slide frame with respect to said frame.

13. A jig according to claim 1, wherein said detachable unit comprises a fitting portion fitted in a headrest mount of the top plate, and a frame attached to said fitting portion and crossing the top plate.

14. A jig according to claim 13, wherein said detachable unit comprises a slide frame attached to said frame and configured to slide in a widthwise direction of the top plate, and wherein said rotating unit is attached to said slide frame.

15. A jig according to claim 14, further comprising a fixing unit configured to stop a sliding of said slide frame with respect to said frame.

16. A jig according to claim 1, wherein said detachable unit comprises a fitting portion fitted in a headrest mount of the top plate, and said rotating unit is attached to said fitting portion.

17. A bed included in a medical image device having at least one operational component, comprising:
    an elevating mechanism configured to elevate a top plate of said top plate;
    a slide mechanism configured to slide said top plate; and an exchange jig detachably attached to said top plate, said exchange jig having a detachable unit configured to be detachably coupled to the top plate, a rotating unit attached to said detachable unit and configured to rotate about an axis substantially perpendicular to an axis parallel to the top plate, and an arm unit attached to said rotating unit, wherein the elevating and slide mechanisms move the exchange jig such that the arm unit operates as a lift to exchange the at least one operational component.

18. A bed according to claim 17, wherein said slide mechanism comprises a plurality of main rollers arranged immediately below said top plate, and a plurality of sub-rollers arranged at right and left edges of said top plate in order to reduce a rolling of said top plate.

19. An X-ray computed tomography apparatus, comprising:

a gantry having an X-ray tube and an X-ray detector;

a computer configured to reconstruct tomographic image data based on projection data of an object to be examined that are collected by said gantry;

a bed on which the object to be examined lies, said bed having an elevating mechanism configured to elevate a top plate of the bed and a slide mechanism configured to slide the top plate; and an exchange jig detachably attached to said top plate, said exchange jig having a detachable unit configured to be detachably coupled to the top plate, a rotating unit attached to said detachable unit and configured to rotate about an axis substantially perpendicular to an axis parallel to the top plate, and an arm unit attached to said rotating unit, wherein the elevating and slide mechanisms move the exchange jig such that the arm unit operates as a lift to exchange at least one of the X-ray tube and X-ray detector.

20. A method for exchanging at least one operational component of a X-ray computed tomography apparatus having a bed, the method comprising:

attaching an exchange jig to a top plate of the bed, said exchange jig including a detachable unit configured to be detachably coupled to the top plate, a rotating unit attached to the detachable unit and configured to rotate about an axis substantially perpendicular to an axis parallel to the top plate, and an arm unit attached to said rotating unit; and elevating and sliding the top plate such that the arm unit of the exchange jig operates as a lift to exchange the at least one operational component.

* * * * *